United States Patent [19]

Kjellberg et al.

[11] Patent Number: 4,626,532
[45] Date of Patent: Dec. 2, 1986

[54] PROCESS FOR STABILIZATION OF BACAMPICILLIN HYDROCHLORIDE

[75] Inventors: Ulf A. Kjellberg, Rönninge; Per G. H. Nyqvist, Tullinge; Jan U. Stenhede, Södertälje; Lars B. Stenmark, Karlskoga, all of Sweden

[73] Assignee: Astra Lakemedel Aktieboag, Sodertalje, Sweden

[21] Appl. No.: 792,507

[22] Filed: Oct. 29, 1985

[30] Foreign Application Priority Data

Nov. 9, 1984 [SE] Sweden ................................ 8405611

[51] Int. Cl.⁴ ...................... A61K 31/43; C07D 499/32
[52] U.S. Cl. ..................................... 514/195; 540/315; 540/336
[58] Field of Search ...................... 260/239.1; 514/195

[56] References Cited

U.S. PATENT DOCUMENTS 3,939,270  2/1976  Ekstrom et al. ................. 260/239.1

FOREIGN PATENT DOCUMENTS 0037740  10/1981  European Pat. Off. .
0069097   1/1983  European Pat. Off. .
3132614   5/1982  Fed. Rep. of Germany .
1293590  10/1972  United Kingdom .
2087236   5/1982  United Kingdom .

OTHER PUBLICATIONS

Chemical Abstracts, vol. 55 (1961), abstract No. 20,339b, Czech. 96,618, "Antibiotic Preparations".
Chemical Abstracts, vol. 93 (1980), abstract No. 245,445x, Pol. 106,789, "Stabilization of 6-[D-(-)α(aminophenyl)acetamido]penicillanic Acid Trihydrate".
Chemical Abstracts, vol. 94 (1981), abstract No. 20,395b, Jpn. Kokai Tokkyo Koho 80 87,715, "Stabilized Bacampicillin Hydrochloride Preparations".

*Primary Examiner*—Natalie Trousof
*Assistant Examiner*—Vera C. Clarke
*Attorney, Agent, or Firm*—Brumbaugh, Graves, Donohue & Raymond

[57] ABSTRACT

A new process for the stabilization of bacampicillin hydrochloride against degradation by humidity characterized by the incorporation of between 3 to 9% by weight of straight-chain alkanes, alkenes, fatty acids, alcohols, and esters of fatty acids and alcohols with molecular weights between 144 and 350, which may be carried out in one step together with wetmassing for granulation.

12 Claims, No Drawings

PROCESS FOR STABILIZATION OF BACAMPICILLIN HYDROCHLORIDE

The present invention relates to a new method for stabilization of bacampicillin hydrochloride by treatment with certain straight-chain organic compounds. This treatment may be carried out as part of the wet-massing of bacampicillin hydrochloride to achieve granulation.

STATE OF THE ART

Bacampicillin is the generic name for 1-ethoxycarbonyloxyethyl 6-(D-aminophenylacetamido)penicillanate and has gained widespread use in oral chemotherapy against a number of gram-negative and gram-positive bacteria. It is usually prepared, purified and administered in form of its hydrochloride as described in British Pat. No. 1 363 506.

Bacampicillin hydrochloride purified by solvent extraction exhibits properties undesirable from a manufacturers and users standpoint. Inherent with its mainly microcrystalline nature is dusting which creates industrial hygiene problems. Another unwanted property is its low stability on storage at medium or high humidities.

Dusting has been overcome by agglomeration through wet milling, described in British Pat. No. 1 293 590. Wet milling without need for isolation of solvent-extracted bacampicillin hydrochloride has been disclosed in the Swedish Patent Application No. 8202752-5. A reduction of sensitivity towards water vapour by mixing, eventually in the presence of a solvent later removed by distillation, bacampicillin hydrochloride with between 9.7 and 52% by weight of at least one member selected from the group consisting of fats and oils, fatty acids and their esters, higher alcohols, waxes, and paraffins, has been demonstrated in the Japanese Patent Application No. 161 830/78.

The decomposition of bacampicillin hydrochloride by prolonged exposure to humidity seems to be a rather complex process. The adsorption of water vapour by this substance is followed by hydrolytic processes as shown by the formation of penicilloic acid, but also by other types of reactions indicated by discoloration and formation of a complex mixture of degradation products. Chemical changes are accompanied by deliquescence at an advanced stage of degradation.

General description of the invention

It has now surprisingly been found that protection of bacampicillin hydrochloride against the action of water vapour may be obtained by lower amounts of protecting compounds than previously thought. The use of less protecting material to ensure the same protecting effect on a biologically active substance is advantageous from a pharmacological and economic standpoint. It has also been found that straight-chain members of the following classes of compounds, viz. alkanes, alkenes, aliphatic alcohols, aliphatic carboxylic acids, and esters of aliphatic carboxylic acids with aliphatic alcohols, are especially well suited as protecting compounds and give valuable protection already when added in 3% by weight, and full protection when added at 5 to 9% by weight. As it is especially advantageous to use the minimum amount of protecting compound sufficient for full protection, a content of 5 to 8% by weight of protecting compound, calculated on dry bacampicillin hydrochloride, is preferred. It was furthermore found that compounds most useful for protection belonging to said classes have a molecular weight between 144 and 350 Dalton. Also a mixture of two or more members of one or more of said classes will exhibit a similar effect, as has been shown for cetostearyl alcohol.

It also has now surprisingly been found that the affinity of the protecting compounds for bacampicillin hydrochloride allows the addition of said protecting compounds in a suitable solvent, e.g. ethyl acetate or isopropanol, to bacampicillin hydrochloride, and removal of the solvent by filtration or centrifugation without the protecting compounds being eluted. The protecting compounds are brought into contact with bacampicillin hydrochloride advantageously by wetmassing, whereby both protection and granulation is achieved in one single step. The use of a known hygroscopic granulation agent, such as polyvinylpyrrolidone does not impair storage properties of bacampicillin hydrochloride, nor the addition of a coating agent like ethyl cellulose is required.

We have established that effective protecting compounds essentially must have straight-chains which may be interrupted or terminated by oxygen. We also found that unsaturation and isomery at multiple bonds do not have an adverse effect on protection. Branching or the introduction of an aromatic ring is though deleterious in spite of such inefficient protecting compounds also being adsorbed or absorbed by bacampicillin hydrochloride. The upper limit for the molecular weight of useful compounds is given by accessability of such compounds and their solubility in butyl acetate or isopropanol, which for practical reasons means a molecular weight of about 350. The lower limit in molecular weight for useful compounds is indicated by butyl butyrate and hexyl acetate. Increase in stabilization is observed up to a chain length of 12.

Bacampicillin hydrochloride adsorbs up to 12% (w/w) of the protecting compounds according to the invention. After drying for one hour at 60° in a fluid-bed dryer, stabilized bacampicillin with 5% or more of the protecting compounds contains only minor amounts of residual solvents (ethyl and butyl acetate), typically ca. 1% (w/w) totally. Stabilization increases with the amount of protecting compound added up to a content of about 5% (w/w). An increase of this content above 5% does not seem to further improve stability.

In Table 1 this efficient, unexpected and desirable protection is demonstrated for a number of compounds. It may be explained by taking into consideration the three-dimensional structure of bacampicillin hydrochloride which we have elucidated in detail.

Detailed description of the invention

Bacampicillin hydrochloride is known to exist in two diastereomeric forms, the S-epimer and the R-epimer. Both are obtained in admixture by the industrial processes for its preparation presently known. The S-epimer forms trigonal crystals, but the R-epimer is only obtained in amorphous form.

Bacampicillin hydrochloride is industrially purified by precipitation from its aqueous solution by addition of butyl acetate and sodium chloride followed by filtration and washing with ethyl acetate. The precipitate consists of microcrystalline S-epimer, on the surface of which R-epimer is co-precipitated in varying amounts. The precipitate is then eventually granulated with ethyl acetate as granulation liquid. The granulate is air-dried but nonetheless contains substantial amounts of the two solvents used, viz. ethyl and butyl acetate (it should be noted that both ethyl acetate and butyl acetate are lower homologues to one class of compounds claimed in this application, viz. straightchain esters of aliphatic alcohols, and that their behaviour towards bacampicillin hydrochloride fits well with the explanation of protective behaviour given below). They may only be removed by drying under vacuum with heating. Ethyl acetate has been found to be removed with greater ease than butyl acetate. Initial solvent contents correspond to about one molecule of solvent being adsorbed per crystal unit cell. Bacampicillin hydrochloride preparations rich in S-epimer retain these solvents more effectively than do preparations rich in R-epimer as shown by differential thermal analysis.

It was furthermore found by X-ray powder diffraction analysis that the trigonal crystals of the S-epimer have channels with a diameter of about 7 Å along one of the main crystallographic axes. These open channels offer access to water which thereby is able to exert its hydrolytic activity not only at the surface of bacampicillin hydrochloride crystals, but right through them. Appropriate inert organic compounds such as those claimed in the present application may be used for blocking these channels thereby reducing the rate of hydrolytic degradation dramatically. The same effect must also be working in the amorphous phase of the R-epimer because preparations rich in R-epimer have been found to specifically adsorb the claimed protecting compounds in about the same proportions and to be protected by them. This is explained by the fact that R-epimer exclusively co-precipitates on the surface of S-epimer forming a layer not exceeding 800 Å in thickness. The R-epimer adhearing by specific adsorption to the ordered S-epimer may thus be supposed to acquire a semi-ordered state similar in physical properties to the latter.

Stabilized and granulated bacampicillin hydrochloride according to the invention constitutes a valuable ingredient in pharmaceutical compositions for oral administration and confers upon them resistance to degradation by moisture. These pharmaceutical compositions will be administered in any of the usual dosage forms such as tablets, capsules, powders, suspensions, sustained-release preparations, and the like and can also contain other adjuvants, modifiers, carriers, excipients, and lubricants.

The preferred stabilizing agents in accordance with the invention are cetyl alcohol and cetostearyl alcohol. Particularly preferred are they in an amount of 6% by weight calculated on dry bacampicillin hydrochloride.

The following examples illustrate the invention.

EXAMPLE 1

(Method A). A planetary mixer was charged with 650 g of a mixture of bacampicillin hydrochloride (500 g), butyl acetate and ethyl acetate. To this mixture 120 g of a solution of one part by weight of one of the substances listed under "Method A" in Table 1 in two parts of isopropanol or ethyl acetate was added followed by wetmassing for 5 min. The resulting granulate was transferred to a wet mill, milled and dried in a fluid bed drier for 1 hour at 60° C. Drymilling in an oscillating granulator with screen width of 1.2 mm resulted in a white granulate containing between 5.3 and 6.9% by weight of the stabilizing substance.

EXAMPLE 2

(Method B). A planetary mixer was charged with 140 g of a mixture of bacampicillin hydrochloride (100 g), butyl acetate and ethyl acetate. To this mixture was added 26 g of a solution prepared by dissolving one part by weight of one of the substances listed under "Method B" in Table 1 in three parts of ethyl acetate and the mixture wetmassed for 5 min. The granulate was then screened through a 4 mm screen and dried in a drying oven at 60° C. for one hour. Drymilling in an oscillating granulator with screen width 1.0 mm resulted in a granulate containing about 6% by weight of the stabilizing substance.

EXAMPLE 3

A planetary mixer was charged with 640 g of a mixture of bacampicillin hydrochloride (500 g), butyl acetate and ethyl acetate. A solution of cetyl alcohol in isopropanol (1+2, w/w) was added and the mixture wet massed for 5 to 15 min. The quantity of cetanol solution added in three separate experiments was 45 g, 90 g and 135 g, respectively. After milling in a wet mill (Alexanderwerk, FRG.) the coarse granulate was dried for 60 min at 60° C. in a fluid bed dryer and then drymilled in an oscillating granulator (Frewitt) with screen width 1.2 mm. The resulting granulates contained 3.1, 6.1, and 8.8 % of cetyl alcohol.

EXAMPLE 4

(Method C). The granules obtained in Example 3 with 90 g of cetanol solution were transferred to a double cone mixer. To this 29 g of microcrystalline cellulose powder, 29 g of croscarmellose sodium and 7.6 g of magnesium stearate were admixed. The mixture was compressed to tablets with a weight of 483 mg. Reference tablets were prepared from bacampicillin hydrochloride treated with isopropanol instead of cetanol.

EXAMPLE 5

A planetary mixer was charged with 3 200 g of a mixture of bacampicillin hydrochloride (2 368 g), butyl acetate and ethyl acetate. A solution of cetyl alcohol (142 g) and polyvinylpyrrolidone (59 g) in isopropanol (270 g) was added. After wetmassing the contents were transferred to a wet mill, milled and dried at 60° C. for one hour in a fluid bed dryer. The granules were screened in an oscillating granulator with screen width 1.2 mm. As reference, two portions of 3 200 g of the same mixture of bacampicillin hydrochloride with butyl acetate and ethyl acetate were granulated with isopropanol (400 g) and with a solution of cetyl alcohol (142 g) in isopropanol (270 g), respectively. The same procedure as above was followed. These three preparations were tested for stability at 75% humidity and 25° C. After 35 days of storage the cetanol and cetanol-PVP preparations contained between 71 and 72% bacampicillin whereas the reference then had completely decomposed.

EXAMPLE 6

(Method D). A planetary mixer was charged with 550 g of a mixture of bacampicillin hydrochloride (500 g), butyl acetate and ethyl acetate. A solution of one of the compounds described in Table 1 under Method D in ethyl acetate or isopropanol (1:3, by weight) was prepared and from this solution 120 g added to the wet bacampicillin hydrochloride. Further processing as described in Example 1. The granulate so obtained contained between 5.3 and 6.7% (w/w) of the respective compound.

EXAMPLE 7

Bacampicillin hydrochloride suspended in butyl acetate was charged into a centrifuge. The wet powder bed, corresponding to about 60 kg dry bacampicillin hydrochloride, was washed with 200 liters of butyl acetate (40° C.) in the centrifuge at constant centrifugation. Hereafter a solution of 14% (w/w) cetanol in butyl acetate (40° C.) was sprayed onto the wet powder mass. Spraying was continued until butyl acetate leaving the centrifuge contained 14% of cetanol. 175 kg of cetanol were used. Centrifugation was then continued for 45 minutes before discharging. The wet powder mass was charged into a planetary mixer and wet massed for 10 minutes with addition of a further 5.6 kg of the cetanol solution. Wetmilling was performed in an Alexanderwerk wetgrinding mill followed by drying in a fluid bed dryer (Aeromatic) for 4 h at 60° C. The dried mass was finally screened in an oscillating granulator (Frewitt) with a 1.2 mm screen.

ing of alkanes, alkenes, esters of aliphatic alcohols with aliphatic carboxylic acids, aliphatic alcohols, and aliphatic carboxylic acids, characterized in that said protecting substance has a straight chain which may be interrupted or terminated by oxygen, and has a molecular weight between 144 and 350 Dalton, and is present in bacampicillin hydrochloride in 3 to 9% by weight, calculated on dry bacampicillin hydrochloride.

2. Bacampicillin hydrochloride protected from degradation by storage in the presence of water vapour according to claim 1, characterized in that protection is effected by a mixture of two or more of said protecting substances.

3. Bacampicillin hydrochloride protected from degradation by storage in the presence of water vapour according to claim 1 or 2, characterized in that it contains a granulating agent.

4. Bacampicillin hydrochloride protected from degradation by storage in the presence of water vapour according to claim 1 or 2, characterized in that it is a mixture of S-epimer and R-epimer, the latter deposited on the former in layers not exceeding 800 Å.

5. Bacampicillin hydrochloride protected from deg-

TABLE 1

Bacampicillin hydrochloride and corresponding penicilloic acid in bacampicillin hydrochloride preparations stabilized by about 6% of different organic compounds, before and after storage for different periods of time at 25° C. and 75% relative humidity.

| substance | Production method$^{xx}$ | Bacampicillin hydrochloride (%) | | | | | Penicilloic acid (%) | | | | |
|---|---|---|---|---|---|---|---|---|---|---|---|
| | | 0 | 6 | 13 (12)$^x$ | 18 | 40 days | 0 | 6 | 13 (12)$^x$ | 18 | 40 days |
| Myristyl alcohol ∅ | A | 91.8 | 88.6 | 80.4 | — | 71.1 | 0.4 | 2.5 | 6.7 | — | 21.0 |
| Cetyl alcohol ∅ | A | 91.2 | 89.6 | 83.7 | 83.0 | 73.9 | 0.7 | 2.5 | 6.1 | 8.2 | 17.4 |
| Stearyl alcohol ∅ | A | 91.8 | 86.9 | 79.1 | — | 73.7 | 0.5 | 3.0 | 7.4 | — | 18.6 |
| Cetostearyl alcohol** ∅ | A | 89.3 | 86.7 | 81.3 | — | 68.7 | 1.2 | 3.4 | 6.9 | — | 20.9 |
| Mytristic acid ∅ | A | 92.2 | 86.3 | 77.9 | — | 70.4 | 0.6 | 3.9 | 7.6 | — | 22.7 |
| Palmitic acid ∅ | A | 91.9 | 85.8 | 78.1 | — | 70.8 | 0.4 | 3.7 | 7.6 | — | 21.9 |
| Stearic acid ∅ | A | 90.4 | 86.6 | 82.0 | — | 75.2 | 0.5 | 3.0 | 5.1 | — | 16.3 |
| Hexyl acetate ∅ | A | 95.5 | 87.4 | 82.0 | 73.9 | 58.8 | 0.4 | 3.7 | 8.3 | 14.9 | 36.7 |
| Ethyl hexanoate ∅ | A | 91.2 | 88.2 | 83.0 | — | 50.8 | 0.8 | 3.0 | 8.3 | — | 40.0 |
| Octyl acetate ∅ | A | 95.1 | 89.9 | 87.4 | 84.8 | 81.3 | 0.6 | 2.1 | 3.8 | 4.8 | 13.8 |
| Dodecyl acetate ∅ | A | 92.8 | 89.7 | 88.9 | 83.4 | 84.4 | 0.4 | 1.5 | 2.4 | 2.6 | 8.4 |
| Ethyl dodecylate ∅ | A | 91.2 | 89.5 | 87.4 | 84.5 | 82.5 | 0.3 | 1.0 | 2.7 | 5.4 | 8.7 |
| Butyl butyrate ∅ | A | 96.5 | 88.3 | 81.2 | — | 66.5 | 0.7 | 3.4 | 8.9 | — | 29.8 |
| Octyl butyrate ∅ | A | 95.3 | 91.1 | 86.1 | 83.2 | 84.7 | 0.6 | 1.5 | 3.4 | 6.0 | 10.6 |
| Allyl heptanoate ∅ | A | 93.6 | 91.1 | 87.9 | 82.3 | 76.2 | 0.6 | 2.5 | 4.9 | 8.7 | 17.4 |
| Dodecane ∅ | B | 91.0 | 89.0 | 86.6$^x$ | 85.1 | — | 0.1 | 1.0 | 2.8$^x$ | 4.8 | — |
| Tetradecane ∅ | B | 90.6 | 88.6 | 86.4$^x$ | 85.5 | — | 0.1 | 0.8 | 2.4$^x$ | 4.3 | — |
| Hexadecane ∅ | B | 90.3 | 89.8 | 86.2$^x$ | 85.6 | — | 0.4 | 0.9 | 2.6$^x$ | 4.1 | — |
| Octadecane ∅ | B | 89.5 | 87.0 | 85.8$^x$ | 84.4 | — | 0.4 | 1.3 | 3.2$^x$ | 5.4 | — |
| Oleinic acid ∅ | B | 89.0 | 85.6 | 82.1$^x$ | 80.3 | — | 0.3 | 2.2 | 5.0$^x$ | 7.6 | — |
| Elaidinic acid ∅ | B | 91.6 | 86.1 | 81.6$^x$ | 79.3 | — | 0.2 | 2.6 | 6.6$^x$ | 9.2 | — |
| 5-Eicosanol | B | 90.2 | 84.8 | 81.9$^x$ | 76.1 | — | 0.2 | 3.3 | 7.2$^x$ | 12.8 | — |
| 5-Butyl -5-eicosanol | B | 87.8 | 80.3 | 71.5$^x$ | 65.2 | — | 0.1 | 5.5 | 11.2$^x$ | 18.8 | — |
| Cetyl alcohol ∅ | B | 89.2 | 86.1 | 83.3$^x$ | 79.9 | — | 0.4 | 1.8 | 4.8$^x$ | 8.6 | — |
| Cetyl alchol tablets ∅ | C | 100 | — | — | 99.5 | **** | 0.1 | — | — | 0.6 | ***** |
| Reference tablets*** | C | 100 | 76.0* | 51.3$^x$ | —* | —* | 0.1 | 7.7* | 14.1* | —* | —* |
| 2'-Ethylhexyl 2-propyl-pentanoate | B | 89.0 | 72.1 | —* | —* | — | 0.2 | 12.4 | —* | —* | — |
| 2-Ethylhexyl acetate | D | 79.9 | —* | —* | —* | — | 2.8 | —* | —* | —* | — |
| Ethylphenylacetate | D | 94.9 | 85.1* | —* | —* | — | 0.4 | 4.9* | —* | —* | — |
| β-Phenylethyl acetate | D | 96.0 | 89.0 | 80.3$^x$ | —* | — | 0.6 | 1.8 | 9.6 | —* | — |
| β-Phenylethyl phenylacetate | D | 93.9 | 84.8* | —* | —* | — | 0.4 | 4.7* | —* | —* | — |
| Reference*** | A | 93.6 | 65.0 | 58.9 | —* | — | 1.7 | 25.8 | 48.4* | —* | —* |

*Deliquescent
**A number of batches containing between 92.9 and 95.8% cetanol and between 4.0 and 7.0 tetradecanol + octadecanol have been tested with similar results.
***Bacampicillin hydrochloride treated with isopropanol instead of protective compounds.
****43 days 98.0%, 67 days 94.9%.
*****43 days 1.1%, 67 days 1.6%.
xx See under examples 1,2,4 and 6.
∅ Protecting compound according to the invention.

We claim:

1. Bacampicillin hydrochloride protected from degradation by storage in the presence of water vapour by a protecting substance selected from the classes consistradation by storage in the presence of water vapour according to claim 1 or 2, characterized in that the protecting substance is cetyl alcohol.

6. Bacampicillin hydrochloride protected from degradation by storage in the presence of water vapour according to claim 1 or 2, characterized in that the protecting substance is cetostearyl alcohol.

7. Pharmaceutical compositions containing bacampicillin hydrochloride protected from degradation by storage in the presence of water vapour according to claim 1 or 2.

8. A process for the manufacture of bacampicillin hydrochloride protected from degradation by storage in the presence of water vapour characterized in that wetmassing of bacampicillin hydrochloride for the purpose of granulation is carried out in the presence of 3 to 9% by weight, calculated on dry bacampicillin hydrochloride, of at least one straight-chain protecting substance with a molecular weight between 144 and 350 Dalton which may be interrupted or terminated by oxygen and is selected from the classes consisting of alkanes, alkenes, esters of aliphatic alcohols with aliphatic carboxylic acids, aliphatic alcohols, and aliphatic carboxylic acids.

9. A process according to claim 8, characterized in that the bacampicillin hydrochloride is brought into contact with a solution of the protecting substance dissolved in a solvent therefor and the solvent is removed by filtration or centrifugation.

10. A process according to claim 8 or 9, characterized in that the protecting substance is cetyl alcohol.

11. A process according to claim 8 or 9, characterized in that the protecting substance is cetostearyl alcohol.

12. Pharmaceutical compositions containing bacampicillin hydrochloride, characterized in that said bacampicillin hydrochloride has been granulated and protected by a process according to claim 8 or 9.

* * * * *